(12) United States Patent
Uyama et al.

(10) Patent No.: US 6,797,010 B2
(45) Date of Patent: Sep. 28, 2004

(54) REDEPOSITION OR BACKSTAIN INHIBITION DURING STONEWASHING PROCESS

(75) Inventors: Naoto Uyama, Chiba-prefecture (JP); Kosaku Daimon, Chiba-ken (JP)

(73) Assignee: Novozymes A/S, Bagsvaerd (DK)

(*) Notice: Subject to any disclaimer, the term of this patent is extended or adjusted under 35 U.S.C. 154(b) by 126 days.

(21) Appl. No.: 09/924,379

(22) Filed: Aug. 8, 2001

(65) Prior Publication Data

US 2002/0066144 A1 Jun. 6, 2002

Related U.S. Application Data

(63) Continuation of application No. PCT/DK01/00384, filed on Jun. 5, 2001.
(60) Provisional application No. 60/211,004, filed on Jun. 12, 2000, provisional application No. 60/244,351, filed on Oct. 30, 2000, provisional application No. 60/253,798, filed on Nov. 29, 2000, and provisional application No. 60/265,473, filed on Jan. 31, 2001.

(30) Foreign Application Priority Data

| Jun. 2, 2000 | (DK) | 2000 00861 |
|---|---|---|
| Oct. 23, 2000 | (DK) | 2000 01577 |
| Nov. 24, 2000 | (DK) | 2000 01772 |
| Jan. 19, 2001 | (DK) | 2001 00100 |

(51) Int. Cl.$^7$ .............................................. D06M 0/00
(52) U.S. Cl. ......................... 8/115.51; 8/137; 510/320; 510/321; 510/392; 510/393
(58) Field of Search .............................. 8/115.51, 137; 510/320, 321, 392, 393

(56) References Cited

U.S. PATENT DOCUMENTS 5,837,010 A * 11/1998 Baeck et al. .................. 8/137
5,912,157 A    6/1999 von der Osten

FOREIGN PATENT DOCUMENTS

| WO | WO 93/25655 | 12/1993 |
|---|---|---|
| WO | WO 94/07983 | 4/1994 |
| WO | WO 94/29426 | 12/1994 |
| WO | WO 97/04160 | 2/1997 |
| WO | WO 99/51808 | 10/1999 |

* cited by examiner

Primary Examiner—Charles Boyer
Assistant Examiner—Derrick G. Hamlin
(74) Attorney, Agent, or Firm—Elias J. Lambiris

(57) ABSTRACT

The present invention relates to the inhibition of backstaining or redeposition during the stonewashing process by applying a lipolytic enzyme, preferably cutinase, thereby avoiding that the blue color redeposits on the fabric or garment.

8 Claims, No Drawings

REDEPOSITION OR BACKSTAIN INHIBITION DURING STONEWASHING PROCESS

CROSS-REFERENCE TO RELATED APPLICATIONS

This application is a continuation application of PCT/DK01/00384 filed Jun. 5, 2001 (the international application was published under PCT Article 21(2) in English) and claims, under 35 U.S.C. 119, priority or the benefit of Danish application nos. PA 2000 00861, PA 2000 01577, PA 2000 01772 and PA 2001 00100 filed Jun. 2, 2000, Oct. 23, 2000, Nov. 24, 2000 and Jan. 19, 2001, respectively, and U.S. provisional application Ser. Nos. 60/211,004, 60/244,351, 60/253,798, and 60/265,473 filed on Jun. 12, 2000, Oct. 30, 2000, Nov. 29, 2000, and Jan. 31, 2001 respectively, the contents of which are fully incorporated herein by reference.

FIELD OF INVENTION

The present invention relates to compositions and methods for reducing or preventing the backstaining of dye on textile materials, especially indigo on denim and specially the backstaining of pocket parts of denim during the stonewashing of denim fabric.

BACKGROUND OF THE INVENTION

By stonewashing of denim the usually blue-dyed denim is given a faded or worn appearance with the characteristic white and blue contrast. Stonewashing the denim material is typically carried out in the presence of purmice stone or cellulase or a combination thereof and results in the removal of dye to give areas of lighter color. The use of cellulase instead of purmice stone has the advantages that it is more environmental friendly, more economical and prevents that the denim is damage because of the rough treatment with the purmice stones. However, the use of cellulase is not without disadvantages.

The dye removed from the denim material after the treatment with cellulase or by a conventional washing process may cause "backstaining" or "redeposition" onto the denim material, e.g. re-coloration of the blue threads and blue coloration of the white threads, resulting in a less contrast between the blue and white threads. In order to remove the dye the denim manufactures are using huge amount of surfactants to make parts white again at a soaping process with heavy washing condition. The heavy washing condition causes color change or color-fading problems for finished denim products. Also additional water has to be used in the subsequent soaping process.

The problem of redeposition or backstaining of dye during stonewashing has also been addressed by adding anti-redeposition chemicals, such as surfactants or other agents into the cellulase wash. Also the use of different cellulases with less specific activity on denim has been tried. WO-A-9407983 describes the use of a cellulase to inhibit the backstaining of denim. WO-A-9429426 and WO-A-9325655 describes backstain inhibition by treatment with a redoposition cellulase composition and added protease as an improvement over the use of redeposition cellulase alone.

Although, these methods aim to solve the problem with the backstaining or redeposition of dye onto the denim material, they may still be improved. In particular, the backstaining or redeposition of dye onto the pocket parts of the denim material poses a problem.

SUMMARY OF THE INVENTION

We have developed a process for treating fabric, especially indigo-dyed denim, with a composition comprising a lipolytic enzyme.

This treatment reduces the risk of back-staining (redeposition of dye onto textile) even when less water is used. The enzymatic treatment of released dyestuff will decrease process time as well as the amount of energy and water needed to achieve a satisfactory quality of the textile, and the color of the wastewater is reduced.

The method of the invention can result in a decreased number of washes, thereby increasing the productivity and decreasing the consumption of water and chemicals, including surfactants.

Accordingly, the present invention provides a method for reducing the backstaining of fabric or textile, comprising contacting the fabric or textile with a composition comprising an effective amount of a lipolytic enzyme (EC 3.1.1).

In another aspect, the present invention relates to a stonewashing composition comprising a lipolytic enzyme and a cellulase.

In a third aspect, the invention relates to the use of the composition for reducing backstaining of fabric or textile.

DETAILED DISCLOSURE OF THE INVENTION

Denim that is stonewashed with the addition of an effective amount of added lipolytic enzyme during cellulase treatment shows a reduction in the level of backstaining, especially the backstaining of pocket parts.

The method of the present invention comprises contacting the denim to be enzymatically stonewashed with a composition comprising the lipolytic enzyme in a amount sufficient to reduce backstaining and thus, to decrease the blue-coloring of e.g. the pocket parts.

The amount of added lipolytic enzyme depends upon others on the purity and amount of cellulase used in the stonewashing process, the contact time, the amount of dye removed during stonewashing, the activity of the cellulase, the pH and temperature of the stonewashing process, the formulation of the product and the like.

The composition to be added may further comprise various adjuvants as known to the skilled person, e.g. surfactants. Other materials can also be used with the composition as desired, including stones, fillers, solvents, buffers, pH control agents, enzyme activators, builders, enzyme stabilizers, other anti-deposition agent and the like. The composition may be formulated at a solid product, granular product or as a liquid product.

The lipolytic enzyme may be added to the composition containing the cellulase for use in stonewashing process or added directly to the stonewashing bath or to a subsequent rinse treatment. The lipolytic enzyme may also be added to a composition for washing purposes thereby reducing or inhibiting the backstaining of removed dye during the washing process.

Fabrics

The process of the present invention applies to fabrics in general. In the context of this invention fabrics include fabrics or textiles prepared from man-made fibers, e.g. polyester, nylon, etc., as well as cellulosic fabrics or textiles.

The term "cellulosic fabric/textile" indicates any type of fabric, in particular woven fabric, prepared from a cellulose-containing material, containing cellulose or cellulose derivatives, e.g. from wood pulp, and cotton. The main part of the cellulose or cellulose derivatives present on the fabric is normally size with which the yarns, normally warp yarns, have been coated prior to weaving. In the present context, the term "fabric" is also intended to include garments and other types of processed fabrics. Examples of cellulosic fabric is cotton, viscose (rayon); lyocell; all blends of viscose, cotton or lyocell with other fibers such as polyester; viscose/cotton blends, lyocell/cotton blends, viscose/wool blends, lyocell/wool blends, cotton/wool blends; flax (linen), ramie and other fabrics based on cellulose fibers, including all blends of cellulosic fibers with other fibers such as wool, polyamide, acrylic and polyester fibers, e.g. viscose/cotton/polyester blends, wool/cotton/polyester blends, flax/cotton blends etc. The fabric may also include man-made fibers alone such as polyester fibers.

The process of the invention is preferably applied to cellulose-containing fabrics, such as cotton, viscose, rayon, ramie, linen or mixtures thereof, or mixtures of any of these fibers with synthetic fibers. In particular, the fabric may be denim. The fabric may be dyed with vat dyes such as indigo, direct dyes such as Direct Red 185, sulfur dyes such as Sulfur Green 6, or reactive dyes fixed to a binder on the fabric surface. In a preferred embodiment of the present process, the fabric is indigo-dyed denim, including clothing items manufactured therefrom.

In a most preferred embodiment, the fabric subjected to the process of the invention is made of hydrophobic fibres such as polyamide fibres, e.g. nylon, acrylic fibres, vinylon and polyester fibres. As mention above the fabric may be made of mixtures of different fibres. Especially contemplated is polyester or polyester/cotton mixtures, which are the material used for pocket parts of garments, in particular dyed cotton garments or denim jeans.

Enzyme

The enzymatic process of the invention may be accomplished using any carboxylic ester hydrolases, in particular lipolytic enzyme and/or any biopolyester hydrolytic enzyme. Such enzymes are well known and defined in the literature, cf. e.g. Borgström B and Brockman H L, (Eds.); *Lipases*; Elsevier Science Publishers B. V., 1984, and Kolattukudy P E; *The Biochemistry of Plants*, Academic Press Inc., 1980, 4 624–631.

In the context of this invention lipolytic enzymes are classified in E.C. 3.1.1 and include true lipases, esterases, phospholipases, and lyso-phospholipases. More specifically the lipolytic enzyme may be a lipase as classified by EC 3.1.1.3, EC 3.1.1.23 and/or EC 3.1.1.26, an esterase as classified by EC 3.1.1.1, EC 3.1.1.2, EC 3.1.1.6, EC 3.1.1.7, and/or EC 3.1.1.8, a phospholipase as classified by EC 3.1.1.4 and/or EC 3.1.1.32, a lyso-phospholipase as classified by EC 3.1.1.5 and a cutinase as classified in EC 3.1.1.74.

The lipolytic enzyme preferably is of microbial origin, in particular of bacterial, of fungal or of yeast origin.

In a particular embodiment, the lipolytic enzyme used may be derived from a strain of Absidia, in particular *Absidia blakesleena* and *Absidia corymbifera*, a strain of Achromobacter, in particular *Achromobacter iophagus*, a strain of Aeromonas, a strain of Alternaria, in particular *Altemaria brassiciola*, a strain of Aspergillus, in particular *Aspergillus niger* and *Aspergillus flavus*, a strain of Achromobacter, in particular *Achromobacter iophagus*, a strain of Aureobasidium, in particular *Aureobasidium pullulans*, a strain of Bacillus, in particular *Bacillus pumilus*, *Bacillus strearothermophilus* and *Bacillus subtilis*, a strain of Beauveria, a strain of Brochothrix, in particular *Brochothrix thermosohata*, a strain of Candida, in particular *Candida cylindracea* (*Candida rugosa*), *Candida paralipolytica*, *Candida tsukubaensis*, *Candida auriculariae*, *Candida humicola*, *Cadida foliarum*, *Candida cylindracea* (*Cadida rugosa*) and *Candida antarctica*, a strain of Chromobacter, in particular *Chromobacter viscosum*, a strain of Coprinus, in particular *Coprinus cinerius*, a strain of Fusarium, in particular *Fusarium oxysporum*, *Fusarium solani*, *Fusarium solani pisi*, and *Fusarium roseum culmorum*, a strain of Geotricum, in particular *Geotricum penicillatum*, a strain of Hansenula, in particular *Hansenula anomala*, a strain of Humicola, in particular *Humicola brevispora*, *Humicula lanuginosa*, *Humicola brevis* var. *thermoidea*, and *Humicola insolens*, a strain of Hyphozyma, a strain of Lactobacillus, in particular *Lactobacillus curvatus*, a strain of Metarhizium, a strain of Mucor, a strain of Paecilomyces, a strain of Penicillium, in particular *Penicillium cyclopium*, *Penicillium crustosum* and *Penicillium expansum*, a strain of Pseudomonas in particular *Pseudomonas aeruginosa*, *Pseudomonas alcaligenes*, *Pseudomonas cepacia* (syn. *Burkholderia cepacia*), *Pseudomonas fluorescens*, *Pseudomonas fragi*, *Pseudomonas maltophilia*, *Pseudomonas mendocina*, *Pseudomonas mephitica lipolytica*, *Pseudomonas alcaligenes*, *Pseudomonas plantari*, *Pseudomonas pseudoalcaligenes*, *Pseudomonas putida*, *Pseudomonas stutzeri*, and *Pseudomonas wisconsinensis*, a strain of Rhizoctonia, in particular *Rhizoctonia solani*, a strain of Rhizomucor, in particular *Rhizomucor miehei*, a strain of Rhizopus, in particular *Rhizopus japonicus*, *Rhizopus microsporus* and *Rhizopus nodosus*, a strain of Rhodosporidium, in particular *Rhodosporidium toruloides*, a strain of Rhodotorula, in particular *Rhodotorula glutinis*, a strain of Sporobolomyces, in particular *Sporobolomyces shibatanus*, a strain of Thermomyces, in particular *Thermomyces lanuginosus* (formerly *Humicola lanuginosa*), a strain of Thiarosporella, in particular *Thiarosporella phaseolina*, a strain of Trichoderma, in particular *Trichoderma harzianum*, and *Trichoderma reesei*, and/or a strain of Verticillium.

In a more preferred embodiment, the lipolytic enzyme used according to the invention is derived from a strain of Aspergillus, a strain of Achromobacter, a strain of Bacillus, a strain of Candida, a strain of Chromobacter, a strain of Fusarium, a strain of Humicola, a strain of Hyphozyma, a strain of Pseudomonas, a strain of Rhizomucor, a strain of Rhizopus, or a strain of Thermomyces.

In a more preferred embodiment, the lipolytic enzyme used according to the invention is derived from a strain of *Bacillus pumilus*, a strain of *Bacillus stearothermophilus* a strain of *Candida cylindracea*, a strain of *Candida*

*antarctica*, in particular *Candida antarctica* Lipase B (obtained as described in WO 88/02775), a strain of *Humicola insolens*, a strain of Hyphozyma, a strain of *Pseudomonas cepacia*, or a strain of *Thermomyces lanuginosus*.

In the context of this invention biopolyester hydrolytic enzyme include esterases and poly-hydroxyalkanoate depolymerases, in particular poly-3-hydroxyalkanoate depolymerases. In fact an esterase is a lipolytic enzyme as well as a biopolyester hydrolytic enzyme.

In a more preferred embodiment, the esterase is a cutinase or a suberinase. Also in the context of this invention, a cutinase is an enzyme capable of degrading cutin, cf. e.g. Lin T S & Kolattukudy P E, *J. Bacteriol.* 1978, 133 (2) 942–951, a suberinase is an enzyme capable of degrading suberin, cf. e.g., Kolattukudy P E; *Science* 1980, 208 990–1000, Lin T S & Kolattukudy P E; *Physiol. Plant Pathol.* 1980, 17 1–15, and *The Biochemistry of Plants*, Academic Press, 1980, Vol. 4 624–634, and a poly-3-hydroxyalkanoate depolymerase is an enzyme capable of degrading poly-3-hydroxyalkanoate, cf. e.g. Foster et al., *FEMS Microbiol. Left.* 1994, 118 279–282. Cutinases, for instance, differs from classical lipases in that no measurable activation around the critical micelle concentration (CMC) of the tributyrine substrate is observed. Also, cutinases are considered belonging to a class of serine esterases.

The biopolyester hydrolytic enzyme preferably is of microbial origin, in particular of bacterial, of fungal or of yeast origin.

In a preferred embodiment, the biopolyester hydrolytic enzyme is derived from a strain of Aspergillus, in particular *Aspergillus oryzae*, a strain of Altemaria, in particular *Altemaria brassiciola*, a strain of Fusarium, in particular *Fusarium solani*, Fusarium solani pisi, *Fusarium roseum culmorum*, or *Fusarium roseum sambucium*, a strain of Helminthosporum, in particular *Helminthosporum sativum*, a strain of Humicola, in particular *Humicola insolens*, a strain of Pseudomonas, in particular *Pseudomonas mendocina*, or *Pseudomonas putida*, a strain of Rhizoctonia, in particular *Rhizoctonia solani*, a strain of Streptomyces, in particular *Streptomyces scabies*, or a strain of Ulocladium, in particular *Ulocladium consortiale*. In a most preferred embodiment the biopolyester hydrolytic enzyme is a cutinase derived from a strain of *Humicola insolens*, in particular the strain *Humicola insolens* DSM 1800.

In another preferred embodiment, the poly-3-hydroxyalkanoate depolymerase is derived from a strain of Alcaligenes, in particular *Alcaligenes faecalis*, a strain of Bacillus, in particular *Bacillus megaterium*, a strain of Camomonas, in particular *Camomonas testosteroni*, a strain of Penicillium, in particular *Penicillium funiculosum*, a strain of Pseudomonas, in particular *Pseudomonas fluorescens*, Pseudomonas lemoignei and *Pseudomonas oleovorans*, or a strain of Rhodospirillum, in particular *Thodospirillum rubrum*.

Specific examples of readily available commercial lipases include Lipolase® (WO 98/35026) Lipolase™ Ultra, Lipozyme®, Palatase®, Novozym® 435, Lecitase® (all available from Novozymes A/S).

Examples of other lipases are Lumafast™, Ps. mendocian lipase from Genencor Int. Inc.; Lipomaxm™, *Ps. pseudoalcaligenes lipase* from Gist Brocades/Genencor Int. Inc.; *Fusarium solani* lipase (cutinase) from Unilever; *Bacillus sp.* lipase from Solvay Enzymes. Other lipases are available from other companies.

Process Conditions

In the case of denim textiles (especially indigo-dyed denim), the process according to the invention can be carried out simultaneously with a treatment with cellulase (and optionally pumice) to create a desired worn look by forming local variations in color density, as described in American dye stuff reporter, Sept. 90, D. Kochavi, T. Videbeek and D. Cedroni, Optimizing processing conditions in enzymatic stone washing. The process of the invention can also be carried out simultaneously with enzymatic desizing, i.e. removal of starch size by means of an ?-amylase. In a further aspect, the process is a conventional washing process, wherein the enzyme of the invention is added to a conventional detergent composition.

The process of the invention may be carried out at conventional conditions in a washing machine conventionally used for stone-washing, e.g. a washer-extractor. The enzyme of the invention should be added in an effective amount. By the term "effective amount" is meant the amount sufficient to reduce backstaining as compared to the backstaining effect when not applying the enzyme of the invention. Typical conditions are a temperature of 40–60° C. and a pH of 4.5–7.5. However, the process conditions must be chosen according to the characteristics of the enzyme in question. They are generally in the range 20–100° C., pH 4.5–10.5, typically 30–90° C., pH 4.5–7.5 especially 40–60° C., pH 4.5–6.5. Optionally, convent additives may be used, e.g. a buffer, a surfactant (anionic and/or non-ionic) and/or a polymer (such as PVP, polyacrylate and polyacrylamide).

Materials and Methods

Enzymes:

Cutinase A (Cutinase variant from Humicola Insolens according to U.S. Pat. No. 5,827,719).

Cutinase B (Cutinase variant from Humicola Insolens according to U.S. Pat. No. 5,827,719).

Denimax® 362S (available from Novozymes A/S).

Lipolase® (available from Novozymes A/S).

Lipolase™ Ultra (available from Novozymes A/S).

Cellusoft® L (available from Novozymes A/S)

Lipolytic Activity

The lipolytic activity may be determined using tributyrine as substrate. This method is based on the hydrolysis of tributyrine by the enzyme, and the alkali consumption is registered as a function of time.

One Lipase Unit (LU) is defined as the amount of enzyme which, under standard conditions (i.e. at 30.0° C; pH 7.0; with Gum Arabic as emulsifier and tributyrine as substrate) liberates 1 mmol titrable butyric acid per minute (1 KLU= 1000 LU).

A folder AF 95/5 describing this analytical method in more detail is available upon request to Novozymes A/S, Denmark, which folder is hereby included by reference.

Cellulytic Activity

The cellulytic activity may be measured in endoglucanase units (EGU), determined at pH 6.0 with carboxymethyl cellulose (CMC) as substrate.

A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g. MIVI 3000 from Sofraser, France), thermostated at 40° C. for 30 minutes.

One EGU is defined as the amount of enzyme that reduces the viscosity to one half under these conditions. The amount of enzyme sample should be adjusted to provide 0.01–0.02 EGU/ml in the reaction mixture. The arch standard is defined as 880 EGU/g.

The cellulolytic activity may also be determined in endo-cellulase units (ECU) by measuring the ability of the enzyme to reduce the viscosity of a solution of carboxymethyl cellulose (CMC).

The ECU assay quantifies the amount of catalytic activity present in the sample by measuring the ability of the sample to reduce the viscosity of a solution of carboxymethylcellulose (CMC). The assay is carried out at 40° C.; pH 7.5; 0.1 M phosphate buffer; time 30 min; using a relative enzyme standard for reducing the viscosity of the CMC Hercules 7 LFD substrate; enzyme concentration approx. 0.15 ECU/ml. The arch standard is defined to 8200 ECU/g.

Color Measurement

A Nippon Denshoku's spectrophotometer (SE 2000), which was in accordance with JIS Z8722, ASTM E308, ASTM E313 and ASTM D1925, was used according to the manufacturer's instructions to evaluate the chromaticity using the change in the color space coordinates L*a*b* (CIELAB-system), where as usual:

- L* gives the change in white/black on a scale from 0 to 100, and a decrease in L* means an increase in black color (decrease in white color) and an increase in L* means an increase in white color (decrease in black color).
- a* gives the change in red/green, and a decrease in a* means an increase in green color (decrease in red color), and an increase in a* means an increase in red color (decrease in green color).
- b* gives the change in blue/yellow, and a decrease in b* means an increase in blue color (decrease in yellow color), and an increase in b* means an increase in yellow color (decrease in blue color) (Vide WO 96/12846 NOVO).

The Nippon Denshoku's spectrophotometer (SE 2000) was operated in the L*a*b* color space. The light source was D65 standard light. The software used for evaluation was ColorMate Version 4.05. The illumination and light-receiving conditions of this instrument is 0–450 after spectrum method based on JIS Z-8722 and was calibrated using the white and black tiles. Each result was an average of 4 measurements. Fabric rinsed without enzyme and mediator was measured and the coordinates L*a*b* were calculated and entered as a reference. The coordinates of the samples were then for each of L*, a*, b* calculated as the difference of the average of the measurements on each swatch from the reference value.

The present invention is further illustrated in the following examples, which are not in any way intended to limit the scope of the invention as claimed.

EXAMPLE 1

Comparison of Anti-back Staining Effect Between Cutinase A and Endolase

An Indigo solution was prepared by washing denim with model washing agent. The compositions of model washing agent are as follows:

Sodium dihydrogen phospate: 6.2 g/20 L
Sodium citrate: 5.8 g/20 L
Novasol P: 2.4 g/20 L
Carezyme 1000 L (available from Novozymes A/S): 2.8 g/20 L The washing conditions were as follows:

| | |
|---|---|
| Temperature: | 55° C. |
| Washing Time: | 120 min |
| Enzyme: | Model washing agent |
| Enzyme dosage: | 1 g/L |
| Washing liquor: | Deionized water (3° dH)/20 L |
| Denim: | Kurabo KD511 |
| Bath ratio: | 1:20 |
| Washing machine: | Wascator (FOM71MP-Lab.) |

Swatches (10 cm×10 cm) of polyester and polyester/cotton was washed with the indigo solution (pH=6.5) prepared above with Cutinase A and a cellulase (Denimax® 362S), respectively. The conditions were:

| | |
|---|---|
| Temperature: | 55° C. |
| Washing Time: | 60 min |
| Washing liquor: | Indigo solution (pH = 6.5) |
| Enzymes: | Cutinase A and Endolase (Novozym ® 613, 3090 ECU/g) |
| Enzyme dosage: | 0, 1, 3, 5, 10 mg enzyme protein/L |
| Swatch: | Polyester, Polyester/Cotton |
| Swatch size: | 10 cm × 10 cm |
| Bath ratio: | (Polyester X 2, Polyester/Cotton X 2)/L |
| T-O-M: | 120 rpm |

Results:

TABLE 1

Comparison of anti-back staining effect between Cutinase A and Endolase (L* value)

| Enzyme | Textile | 0 mg/L*[1] | 1 mg/L*[1] | 3 mg/L*[1] | 5 mg/L*[1] | 10 mg/L*[1] |
|---|---|---|---|---|---|---|
| Cutinase A | Polyester | 68.4 +/− 0.8 | 71.6 +/− 0.2 | 75.7 +/− 0.2 | 79.6 +/− 0.4 | 84.0 +/− 0.2 |
| | Polyester/Cotton | 71.8 +/− 0.1 | 71.8 +/− 0.1 | 73.9 +/− 0.1 | 74.5 +/− 0.1 | 76.9 +/− 0.2 |
| Endolase | Polyester | 68.4 +/− 0.8 | 69.6 +/− 0.3 | 68.8 +/− 0.5 | 69.3 +/− 0.4 | 68.6 +/− 0.4 |
| | Polyester/Cotton | 71.8 +/− 0.1 | 72.4 +/− 0.2 | 72.7 +/− 0.2 | 72.1 +/− 0.1 | 72.7 +/− 0.4 |

*[1]Enzyme protein base

The above results show a significant anti-back staining effect on polyester and polyester/cotton of the cutinase compared with the cellulase. The cellulase did not show any anti-back staining effect on the fabric swatches.

EXAMPLE 2
Anti-back Staining Effect of Cutinase A and B and Lipolase.

An Indigo solution was prepared by washing denim with Denimax® 362S in deionised water. The conditions were as follows:

| | |
|---|---|
| Temperature: | 55° C. |
| Washing Time: | 120 mm |
| Enzyme: | Denimax ® 362S |
| Enzyme dosage: | 1 g/L |
| Washing liquor: | Deionized water (3°dH)/20 L |
| Denim: | Kurabo KD511 |
| Bath ratio: | 1:20 |
| Washing machine: | Wasicator (FOM7IMP-Lab) |

Swatches (10 cm×10 cm) of polyester and polyester/cotton was washed with the indigo solution (pH=6.5) prepared above with the cutinases and Lipolase® 100 L (available from Novozymes A/S), respectively. The conditions were:

| | |
|---|---|
| Temperature: | 55° C. |
| Washing Time: | 60 min |
| Washing liquor: | Indigo solution (pH = 6.5) |
| Enzymes: | Cutinase A and B and Lipolase ® 100L, type EX |
| Enzyme dosage: | 0, 10, 30, 50 mg enzyme protein/L (Table 2) and 0, 1, 3, 5 mg enzyme protein/L (Table 3) |
| Swatch: | Polyester and Polyester/Cotton |
| Swatch size: | 10 cm × 10 cm |
| Bath ratio: | (Polyester X 2, Polyester/Cotton X 2)/1L |
| T-O-M: | 120 rpm |

Results:

The above results show an anti-back staining effect on polyester and polester/cotton of the cutinases and the Lipolase.

EXAMPLE 3
Anti-back Staining Effect of Cutinase and Lipases at acid pH Condition An Indigo solution was prepared by washing denim with Cellusoft® L in deionised water. The conditions were as follows:

| | |
|---|---|
| Temperature: | 55° C. |
| Washing Time: | 120 min |
| Enzyme: | Cellusoft ® L |
| Enzyme dosage: | 1 g/L |
| Buffer: | 1 M Acetate buffer (pH = 4.8)/100 ml/20 L |
| Washing liquor: | Deionized water (3° dH)/20 L |
| Denim: | Kurabo KD511 |
| Bath ratio: | 1:20 |
| Washing machine: | Wasicator (FOM71MP-Lab.) |

Swatches (10 cm×10 cm) of polyester and polyester/cotton was washed with the indigo solution (pH=5) prepared above with Cutinase A and B, Lipolase® and Lipolase™ Ultra, respectively. The conditions were:

| | |
|---|---|
| Temperature: | 55° C. |
| Washing Time: | 60 min |
| Washing liquor: | Indigo solution (pH = 5) |
| Enzymes: | Cutinase A and B, Lipolase ® and Lipolase ™ Ultra |
| Enzyme dosage: | 0, 10, 30, 50 and 100 mg enzyme protein/L (Table 4) and 0, 10 and 30 mg enzyme protein/L (Table 5) |
| Swatch: | Polyester, Polyester/Cotton |
| Swatch size: | 10 cm × 10 cm |
| Bath ratio: | (Polyester X 2, Polyester/Cotton X 2)/L |
| T-O-M: | 120 rpm |

TABLE 2

Anti-back staining effect of enzymes on polyester and polyester/cotton (L* value)

| Textile | Enzyme | 0 mg/L*[1] | 10 mg/L*[1] | 30 mg/L*[1] | 50 mg/L*[1] |
|---|---|---|---|---|---|
| Polyester | Cutinase A | 65.4 +/− 0.3 | 84.6 +/− 0.1 | 89.0 +/− 0.0 | 89.7 +/− 0.1 |
| | Cutinase B | 65.7 +/− 0.2 | 88.3 +/− 0.1 | 90.3 +/− 0.2 | 90.8 +/− 0.2 |
| | Lipolase | 65.1 +/− 0.2 | 66.0 +/− 0.4 | 68.1 +/− 0.2 | 69.0 +/− 0.4 |
| Polyester/Cotton | Cutinase A | 67.9 +/− 0.3 | 76.3 +/− 0.2 | 83.3 +/− 0.0 | 84.6 +/− 0.1 |
| | Cutinase B | 68.6 +/− 0.1 | 82.3 +/− 0.1 | 86.7 +/− 0.1 | 86.9 +/− 0.1 |
| | Lipolase | 68.1 +/− 0.3 | 69.2 +/− 0.1 | 71.8 +/− 0.1 | 73.6 +/− 0.2 |

*[1]Enzyme protein base

TABLE 3

Anti-back staining effect of cutinase with low enzyme dosage (L* value)

| Textile | Enzyme | 0 mg/L*[2] | 1 mg/L*[2] | 3 mg/L*[2] | 5 mg/L*[2] |
|---|---|---|---|---|---|
| Polyester | Cutinase A | 63.7 +/− 0.1 | 68.6 +/− 0.5 | 75.9 +/− 0.6 | 81.2 +/− 0.4 |
| | Cutinase B | 63.9 +/− 0.2 | 71.0 +/− 0.1 | 76.3 +/− 0.3 | 79.3 +/− 0.6 |
| Polyester/Cotton | Cutinase A | 64.2 +/− 0.1 | 65.5 +/− 0.2 | 67.5 +/− 0.4 | 71.0 +/− 0.1 |
| | Cutinase B | 64.5 +/− 0.2 | 66.3 +/− 0.2 | 69.7 +/− 0.4 | 72.2 +/− 0.3 |

Results:

TABLE 4

Anti-back staining effect of Cutinase A and B (L* value)

| Enzyme | Textile | 0 mg/L*[1] | 10 mg/L*[1] | 30 mg/L*[1] | 50 mg/L*[1] | 100 mg/L*[1] |
|---|---|---|---|---|---|---|
| Cutinase A | Polyester | 68.8 +/− 0.5 | 74.7 +/− 1.0 | 79.6 +/− 0.2 | 79.9 +/− 0.1 | 82.2 +/− 1.6 |
|  | Polyester/Cotton | 65.3 +/− 0.9 | 66.8 +/− 0.2 | 68.1 +/− 0.6 | 67.5 +/− 1.0 | 69.9 +/− 0.6 |
| Cutinase B | Polyester | 66.7 +/− 0.3 | 80.3 +/− 0.2 | 82.4 +/− 0.6 | 82.7 +/− 0.2 | 81.7 +/− 0.6 |
|  | Polyester/Cotton | 67.4 +/− 0.9 | 69.2 +/− 0.4 | 69.2 +/− 1.0 | 70.6 +/− 0.1 | 70.8 +/− 0.5 |

*[1]Enzyme protein

Results:

TABLE 5

Anti-back staining effect of Cutinase A and B, Lipolase ® and Lipolase ™ Ultra (L* value)

| Textile | Enzymes | 0 mg/L*[1] | 10 mg/L*[1] | 30 mg/L*[1] |
|---|---|---|---|---|
| Polyester | Cutinase A | 68.5+/−0.4 | 77.9+/−0.5 | 81.9+/−0.5 |
|  | Cutinase B | " | 79.6+/−0.9 | 81.5+/−0.3 |
|  | Lipolase ® | " | 80.0+/−0.8 | 81.5+/−0.9 |
|  | Lipolase ™ Ultra | " | 75.5+/−0.4 | 75.6+/−0.4 |
| Polyester/Cotton | Cutinase A | 62.0+/−0.8 | 62.6+/−0.6 | 63.7+/−0.6 |
|  | Cutinase B | " | 63.8+/−0.5 | 64.3+/−0.7 |
|  | Lipolase ® | " | 63.5+/−0.5 | 67.3+/−0.2 |
|  | Lipolase ™ Ultra | " | 63.2+/−0.5 | 65.2+/−0.6 |

The above results show an anti-back staining effect of the cutinases and the lipases on polyester and polyester/cotton at acidic pH.

What is claimed is:

1. A method for reducing the backstaining of a dye on a denim fabric or textile during stonewashing, comprising contacting the denim fabric or textile with a composition comprising an effective amount of a cutinase (EC 3.1.1.74).

2. The method of claim 1, wherein the cutinase is a *Humicola Insolens* cutinase.

3. The method of claim 1, wherein the fabric or textile is made of hydrophobic fibres.

4. The method of claim 1, wherein the fabric or textile is polyester or a polyester/cotton blend.

5. The method of claim 4, wherein the fabric or textile is polyester or polyester/cotton parts of indigo dyed denim.

6. The method of claim 1, wherein the amount of enzyme is 1–100 mg of enzyme protein per I of composition.

7. The method of claim 1, wherein the pH is in the range of 4.5–7.5 and the temperature is in the range of 40–60° C.

8. The method of claim 1, wherein the composition further comprises a cellulase and/or pumice.

* * * * *